United States Patent [19]

Barberet et al.

[11] Patent Number: Plant 5,514

[45] Date of Patent: Jul. 16, 1985

[54] CARNATION NAMED LONCRUSO

[75] Inventors: Nicole Barberet; Yves Ducloux, both of Antibes, France

[73] Assignee: Laboratoire de Physiologie Vegetale de la Londe, La Londe, France

[21] Appl. No.: 516,570

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Chas. W. Rummler

[57] ABSTRACT

A new spray carnation cultivar particularly distinguished by the very light yellow color of its blossoms which are spotted near the tips of its petals with a rather deep red color, the flowers being borne on straight, rather rigid peduncles branching from a srong, upright stem having rather abundant foliage and a tall, vigorous and upright growth habit and a profuse production of blooms during its Spring and Fall blooming seasons.

1 Drawing Figure

BACKGROUND OF THE NEW PLANT

Our new spray carnation is the result of breeding efforts carried on by us at La Londe, Les Maures, France, since 1976 with the object of developing new plants having nice color and good quality of flower stem and plant growth habit. This new plant originated as a seedling produced by our crossing of selected and individually identified plants growing among our stock of spray carnations maintained at La Londe for breeding purposes and this particular seedling was selected by us for propagation and test because of its very delicate yellow coloration and its favorable growth habit. The discovery plant was reproduced by us at La Londe, by means of cuttings, and the results of this reproduction of the parent plant appearing to be quite favorable with respect to retention of the novel characteristics of the parent plant, we continued such propagation through several successive generations, over a period of years, and thereby determined that the novel and distinctive characteristics of the discovery plant are fully retained from generation to generation and appear to be firmly fixed.

DESCRIPTION OF THE DRAWING

Our new spray carnation plant is illustrated by the accompanying photographic drawing which shows, in full color, the upper or spray portion of a typical flowering stem with buds and flowers in various stages of opening. The colors shown are as nearly true to those specified herein as is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 396 M J.

*Pollen parent.*—Stock Plant No. 73 M L 2. These unnamed varieties are individually identified in our permanent records and are maintained in our carnation collection for breeding purposes at La Londe, France.

Classification:

*Botanic.*— *Dianthus caryophyllus.*

*Commerical.*—Spray Carnation.

Form: Tall, erect bush with at least four stems emitted near the ground.

Height: Averaging about 116 cm. at eight months.

Main stem:

*Length.*—Less than 15 cm. due to pinching.

Branching character: Well branched on all stems.

Growth habit: Vigorous, upright and rather rigid.

Foliage:

*Quantity.*—Rather abundant.

*Number of leaves.*—At least 120.

*Leaf size.*—About 8.5 cm. long and 1.1 cm. wide, in average at seventh node.

*Leaf shape.*—Linear with curved margins.

*Texture.*—Leathery.

*Color.*—Upper side — 189A. Under side — 189A.

*Ribs and veins.*—Hardly noticeable.

*Rachis.*—Hardly noticeable.

THE BUD

Size: Medium.

*Diameter.*—About 1.15 cm. in average.

*Length.*—About 2.5 cm. in average.

Shape: Ovoid.

Rate of opening: Normal for carnations.

Color of petals:

*When sepals first divide and when petals begin to unfurl.*—The colors are the same as the petal coloration at full bloom.

Sepals:

*Number.*—5 To 6.

*Shape.*—Joined at the lower part and generally of acute form at the upper portion with sharply pointed apex. The sepals are hooded over the bud and stand up when the flower opens.

*Color.*—Inside — Greenish white. Outside — 143C and 144D.

*Striae.*—Longitudinal.

Calyx:

*Shape.*—Cylindrical to bell-shaped.

*Splitting.*—The calyx does not split.

*Aspect.*—Smooth.

Flower stem:

*Length.*—About 53 cm.

*Character.*—Erect and rather thin.

*Color.*—189A.

THE FLOWER

Blooming habit: Recurrent, blooming profusely at about midseason of the Spring and Fall blooming periods.

Size of bloom: Small.

*Diameter.*—About 5 cm. in average.

*Depth.*—About 4.5 cm. in average.

Borne: In cluster.

Shape:

*When bloom first opens.*—High centered.

*When bloom matures.*—Dome-shaped.

Petalage:

*Number of petals:*—About 50 in average.

*Arrangement.*—Imbricated.

*Form.*—Fan-shaped with very fine serration at the outer edges.

*Texture.*—Soft.

*Appearance.*—Satiny.

*Color.*—Outer Petal: Body — 3D, many marginally spotted with 51C and 59C. Base — Pale greenish yellow. Reverse side — 1D margnially spotted with 51C and 59C. Inside Petal: Body — 3D marginally spotted with 51C and 59C. Base — Pale greenish yellow. Reverse side — 1D spotted with 51C and 59C.

Flower stem:

*Length.*—About 53 cm. (cut at tenth node).

*Character.*—Upright with good strength.

*Color.*—189A.

Fragrance: Hardly perceptible.

Persistence: The flowers hang on and dry.

Lasting quality:

*As cut flower.*—At least ten days in vase keeping.

Disease resistance: Sensible to *Fusarium oxysporum* as observed INRA, Antibes, Alpes-Maritimes, France.

REPRODUCTIVE ORGANS

Stamens:

*Number.*—4 To 5.

*Arrangement.*—Around the pistils.

*Anthers.*—Size: Less than 4 mm. Color: Yellowish white.

*Filaments.*—Color — Yellowish white.

Pistils:

*Number.*—Most often two.

*Styles.*—Color — Yellowish white.

*Stigmas.*—Color — Lightly purplish red.

Character of ovaries: Rather globular and light green.

This new carnation variety most resembles "TONY" (unpatented) but differs from "TONY" in that the spray of the new plant is more gathered around the stem and the color of the flowers is clearer than that of "TONY".

We claim:

1. A new spray carnation cultivar, substantially as herein shown and described, characterized by the very pale yellow coloration of its small blooms which are marginally spotted or streaked with a dark red color and which are produced profusely on a long, strong flowering stem; and by its vigorous and upright growth habit with abundant foliage.

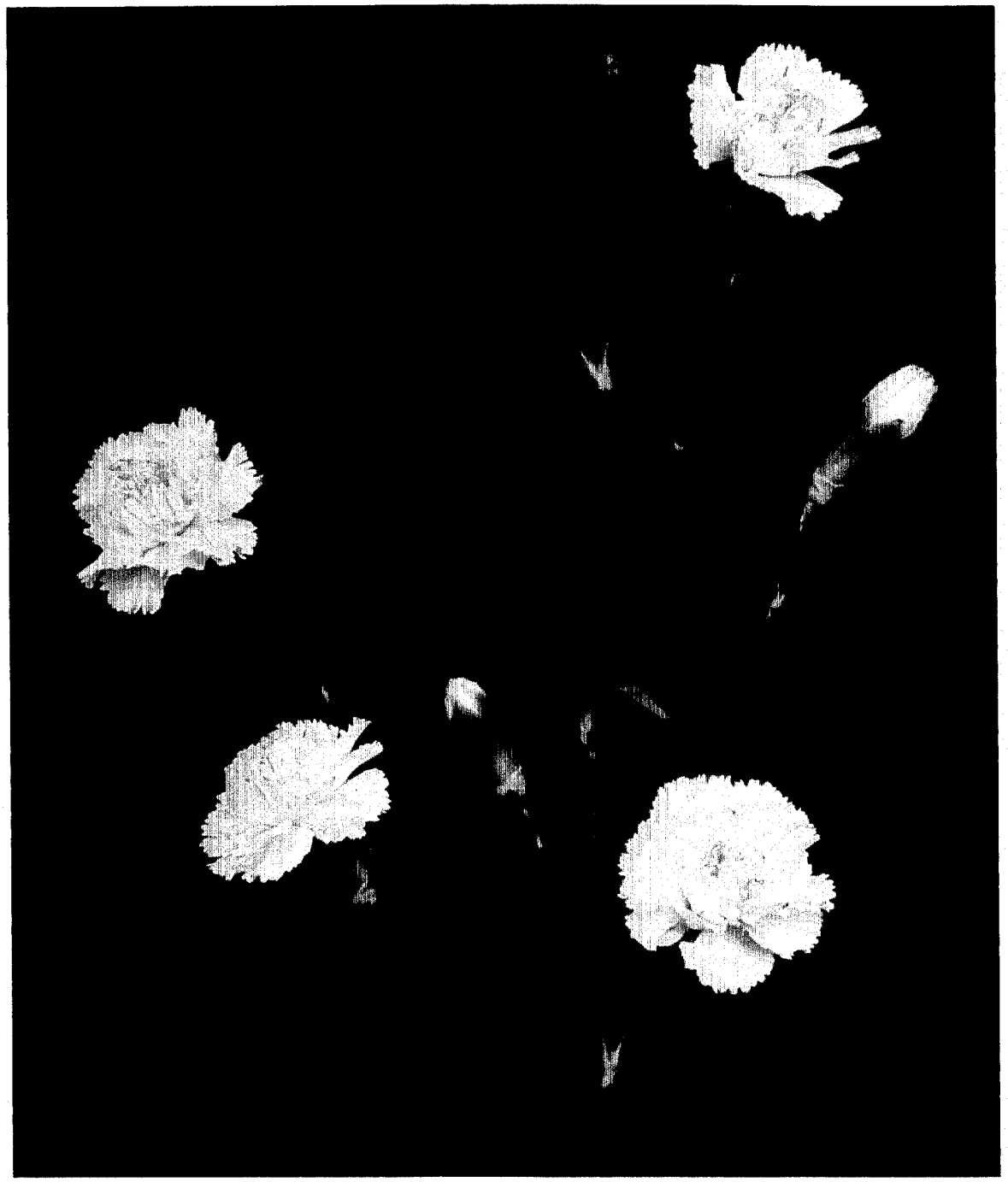

* * * * *